United States Patent
Renauld et al.

(12) 
(10) Patent No.: US 7,033,787 B2
(45) Date of Patent: Apr. 25, 2006

(54) ISOLATED CYTOKINE RECEPTOR LICR-2

(75) Inventors: Jean-Christophe Renauld, Brussels (BE); Helmut Fickenscher, Erlangen-Nurnberg (DE); Laure Dumoutier, Brussels (DE); Simon Hör, Erlangen-Nurnberg (DE)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 10/026,106

(22) Filed: Dec. 21, 2001

(65) Prior Publication Data

US 2003/0158100 A1    Aug. 21, 2003

(51) Int. Cl.
*C12N 15/12* (2006.01)
*C12N 5/10* (2006.01)
*C12N 15/63* (2006.01)
*C12P 21/02* (2006.01)
*C07K 14/47* (2006.01)

(52) U.S. Cl. ............... 435/69.1; 435/71.1; 435/320.1; 435/471; 435/252.3; 435/325; 536/23.5; 530/351

(58) Field of Classification Search ............. 439/69.1, 439/71.1, 320.1, 471, 252.3, 325; 536/23.5; 530/351
See application file for complete search history.

(56) References Cited

FOREIGN PATENT DOCUMENTS

WO    99/61617    12/1999
WO    00/65027    11/2000

OTHER PUBLICATIONS

Calo et al. STAT proteins: from normal control of cellular events to tumorigenesis. J Cell Physiol 197: 157-168, 2003.*
Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223.*
Brenner, S.E. Errors in genome function. Trends in Genetics 15(4): 132-133, 1999.*
Bork et al. Go hunting in sequence but watch out for the traps. Trends in Genetics. 12(10): 425-427, 1996.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Levy et al. What does Stat3 do?. The Journal of Clinical Investigation. May 2002, vol. 109, No. 9, apges 1143-1148.*
Sheppard et al. IL-28, IL-29 and their class II Cytokine receptor IL-28R. Nature Immunology. Jan. 2003, vol. 4, No. 1, apges 63-68.*
Parrish-Novak, et al., "Interleukin-21 and its receptor are involved in NK cell expansion and regulation of lymphocyte function," nature 408:57-63 (Nov. 2, 2000).
Xie, et al., "Interleukin (IL-22), a Novel Human Cytokine That Signals Through the Interleukin Receptor-related proteins CRF 2-4 and IL-22R." J. Biol. Chem 275 (40): 51335-51339 (Oct. 6, 2000).
Dumoutier, et al., "Human interleukin-10-related T cell-derived inducible factor: Molecular cloning and functional characterization as an hepatocyte-stimulating factor." Proc. Natl. Acad Sci USA 97(18); 10144-10149 (2000).

* cited by examiner

*Primary Examiner*—Janet Andres
*Assistant Examiner*—Fozia Hamud
(74) *Attorney, Agent, or Firm*—Fulbright & Jaworski LLP

(57) ABSTRACT

The invention relates to new members of the Class II cytokine receptor family, such as LICR-2. The new member binds to AK155, and mediates STAT activation.

15 Claims, No Drawings

SEQUENCE LISTING

<160> NUMBER OF SEQ ID NOS: 19

<210> SEQ ID NO 1
<211> LENGTH: 21
<212> TYPE: DNA
<213> ORGANISM: Homo sapiens
<220> FEATURE:

<400> SEQUENCE: 1
gggaaccaag gagctgctat g 21

<210> SEQ ID NO 2
<211> LENGTH: 21
<212> TYPE: DNA
<213> ORGANISM: Homo sapiens
<220> FEATURE:

<400> SEQUENCE: 2
tggcactgag gcagtggtgt t 21

<210> SEQ ID NO 3
<211> LENGTH: 20
<212> TYPE: DNA
<213> ORGANISM: Homo sapiens
<220> FEATURE:

<400> SEQUENCE: 3
aaggccatgg cggggcccga 20

<210> SEQ ID NO 4
<211> LENGTH: 20
<212> TYPE: DNA
<213> ORGANISM: Homo sapiens
<220> FEATURE:

<400> SEQUENCE: 4
cagaaggtca gtgtctgaag 20

<210> SEQ ID NO 5
<211> LENGTH: 21
<212> TYPE: DNA
<213> ORGANISM: Homo sapiens
<220> FEATURE:

<400> SEQUENCE: 5
acctgcttct tgctggaggt c 21

<210> SEQ ID NO 6
<211> LENGTH: 21
<212> TYPE: DNA
<213> ORGANISM: Homo sapiens
<220> FEATURE:

<400> SEQUENCE: 6
catcagattc ggtgggatgt c                                                    21

<210> SEQ ID NO 7
<211> LENGTH: 1599
<212> TYPE: DNA
<213> ORGANISM: Homo sapiens
<220> FEATURE:

<400> SEQUENCE: 7
aaggccatgg cggggcccga gcgctggggc cccctgctcc tgtgcctgct gcaggccgct    60
ccagggaggc cccgtctggc ccctccccag aatgtgacgc tgctctccca gaacttcagc   120
gtgtacctga catggctcc cagggcttggc aaccccagg atgtgaccta ttttgtggcc    180
atcagagctc tcccacccgt agacggtggc gcgaagtgga gagtgtgcg ggaaccaagg    240
agctgctatg ttctatgatg tgcctgaaga acaggacct gtacaacaag ttcaagggac    300
gcgtgcggac ggtttctccc agctccaagt cccccctgggt ggagtccgaa tacctggatt   360
acctttttga agtggagccg gccccacctg tcctggtgct cacccagacg gaggagatcc   420
tgagtgccaa tgccacgtac cagctgcccc cctgcatgcc cccactggat ctgaagtatg   480
aggtggcatt ctggaaggag ggggccggaa acaagaccct atttccagtc actccccatg   540
gccagccagt ccagatcact ctccagccag ctgccagcga acaccactgc tcagtgcca    600
gaaccatcta cacgttcagt gtcccgaaat acagcaagtt ctctaagccc acctgcttct   660
tgctggaggt cccagaagcg aactgggctt tcctggtgct gccatcgctt ctgatactgc   720
tgttagtaat tgccgcaggg ggtgtgatct ggaagaccct catggggaac ccctggtttc   780
agcgggcaaa gatgccacgg gccctggact ttttctggaca cacacccct gtggcaacct    840
ttcagcccag cagaccagag tccgtgaatg acttgttcct ctgtcccaa aaggaactga    900
ccagaggggt caggccgacg cctcgagtca gggcccagc cacccaacag acaagatgga   960
agaaggacct tgcagaggac gaagaggagg aggatgagga ggacacagaa gatggcgtca  1020
gcttccagcc ctacattgaa ccaccttctt tcctggggca agagcaccag gctccagggc  1080
actcggaggc tggtggggtg gactcaggga ggcccagggc tcctctggtc caagcgaag   1140
gctcctctgc ttgggattct tcagacagaa gctgggccag cactgtggac tcctcctggg  1200
acagggctgg gtcctctggc tatttggctg agaaggggcc aggccaaggg ccgggtgggg  1260
atgggcacca agaatctctc ccaccacctg aattctccaa ggactcgggt ttcctggaag  1320
agctcccaga agataaccctc tcctcctggg ccacctgggg caccttacca ccggagccga  1380
atctggtccc tggggaccc ccagtttctc ttcagacact gaccttctgc tgggaaagca   1440
gccctgagga ggaagaggag gcgagggaat cagaaattga ggacagcgat gcgggcagct  1500
ggggggctga gagcacccag aggaccgagg acagggccg gacattgggg cattacatgg   1560
ccaggtgagc tgtcccccga catcccaccg aatctgatg                         1599

<210> SEQ ID NO 8
<211> LENGTH: 522
<212> TYPE: PRT
<213> ORGANISM: Homo sapiens
<220> FEATURE:

<400> SEQUENCE: 8

Met Ala Gly Pro Glu Arg Trp Gly Pro Leu Leu Leu Cys Leu Leu Gln
 1               5                  10                  15

-continued

```
Ala Ala Pro Gly Arg Pro Arg Leu Ala Pro Pro Gln Asn Val Thr Leu
            20                  25                  30

Leu Ser Gln Asn Phe Ser Val Tyr Leu Thr Trp Leu Pro Gly Leu Gly
        35                  40                  45

Asn Pro Gln Asp Val Thr Tyr Phe Val Ala Tyr Gln Ser Ser Pro Thr
    50                  55                  60

Arg Arg Arg Trp Arg Glu Val Glu Cys Ala Gly Thr Lys Glu Leu
65                  70                  75                  80

Leu Cys Ser Met Met Cys Leu Lys Lys Gln Asp Leu Tyr Asn Lys Phe
                85                  90                  95

Lys Gly Arg Val Arg Thr Val Ser Pro Ser Ser Lys Ser Pro Trp Val
            100                 105                 110

Glu Ser Glu Tyr Leu Asp Tyr Leu Phe Glu Val Glu Pro Ala Pro Pro
        115                 120                 125

Val Leu Val Leu Thr Gln Thr Glu Glu Ile Leu Ser Ala Asn Ala Thr
    130                 135                 140

Tyr Gln Leu Pro Pro Cys Met Pro Pro Leu Asp Leu Lys Tyr Glu Val
145                 150                 155                 160

Ala Phe Trp Lys Glu Gly Ala Gly Asn Lys Thr Leu Phe Pro Val Thr
                165                 170                 175

Pro His Val Thr Pro His Gly Gln Pro Val Gln Ile Thr Leu Gln Pro
            180                 185                 190

Ala Ala Ser Glu His His Cys Leu Ser Ala Arg Thr Ile Tyr Thr Phe
        195                 200                 205

Ser Val Pro  Lys Tyr Ser Lys Phe Ser Lys Pro Thr Cys Phe Leu Leu
    210                 215                 220

Glu Val Pro Glu Ala Asn Trp Ala Phe Leu Val Leu Pro Ser Leu Leu
225                 230                 235                 240

Ile Leu Leu Leu Val Ile Ala Ala Gly Gly Val Ile Trp Lys Thr Leu
                245                 250                 255

Met Gly Asn Pro Trp Phe Gln Arg Ala Lys Met Pro Arg Ala Leu Asp
            260                 265                 270

Phe Ser Gly His Thr Thr His Pro Val Ala Thr Phe Gln Pro Ser Arg
        275                 280                 285

Pro Glu Ser Val Asn Asp Leu Phe Leu Cys Pro Gln Lys Glu Leu Thr
    290                 295                 300

Arg Gly Val Arg Pro Thr Pro Arg Val Arg Pro Ala Thr Gln Gln Thr
305                 310                 315                 320

Arg Trp Lys Lys Asp Leu Ala Glu Asp Glu Glu Glu Asp Thr Glu
                325                 330                 335

Asp Gly Val Ser Phe Gln Pro Tyr Ile Glu Pro Ser Phe Leu Gly
            340                 345                 350

Gln Glu His Gln Ala Pro Gly His Ser Glu Ala Gly Gly Val Asp Ser
        355                 360                 365

Gly Arg Pro Arg Ala Pro Leu Val Pro Ser Glu Gly Ser Ser Ala Trp
    370                 375                 380

Asp Ser Ser Asp Arg Ser Trp Ala Ser Thr Val Asp Ser Ser Trp Asp
385                 390                 395                 400

Arg Ala Gly Ser Ser Gly Tyr Leu Ala Glu Lys Gly Pro Gly Gln Gly
                405                 410                 415

Pro Gly Gly Asp Gly His Gln Glu Ser Leu Pro Pro Glu Phe Ser
            420                 425                 430
```

| Lys | Asp | Ser | Gly | Phe | Leu | Glu | Glu | Leu | Pro | Glu | Asp | Asn | Leu | Ser | Ser |
|-----|-----|-----|-----|-----|-----|-----|-----|-----|-----|-----|-----|-----|-----|-----|-----|
|     |     | 435 |     |     |     | 440 |     |     |     | 445 |     |     |     |     |     |

| Trp | Ala | Thr | Trp | Gly | Thr | Leu | Pro | Pro | Glu | Pro | Asn | Leu | Val | Pro |
|-----|-----|-----|-----|-----|-----|-----|-----|-----|-----|-----|-----|-----|-----|-----|
| 450 |     |     |     |     | 455 |     |     |     |     | 460 |     |     |     |     |

| Gly | Gly | Pro | Pro | Val | Ser | Leu | Gln | Thr | Leu | Thr | Phe | Cys | Trp | Glu | Ser |
|-----|-----|-----|-----|-----|-----|-----|-----|-----|-----|-----|-----|-----|-----|-----|-----|
| 465 |     |     |     |     | 470 |     |     |     |     | 475 |     |     |     |     | 480 |

| Ser | Pro | Glu | Glu | Glu | Glu | Ala | Arg | Glu | Ser | Glu | Ile | Glu | Asp | Ser |
|-----|-----|-----|-----|-----|-----|-----|-----|-----|-----|-----|-----|-----|-----|-----|
|     |     |     |     | 485 |     |     |     |     | 490 |     |     |     |     | 495 |

| Asp | Ala | Gly | Ser | Trp | Gly | Ala | Glu | Ser | Thr | Gln | Arg | Thr | Glu | Asp | Arg |
|-----|-----|-----|-----|-----|-----|-----|-----|-----|-----|-----|-----|-----|-----|-----|-----|
|     |     |     | 500 |     |     |     |     | 505 |     |     |     |     | 510 |     |     |

| Gly | Arg | Thr | Leu | Gly | His | Tyr | Met | Ala | Arg |
|-----|-----|-----|-----|-----|-----|-----|-----|-----|-----|
|     |     |     |     | 515 |     |     |     | 520 |     |

<210> SEQ ID NO 9
<211> LENGTH: 1469
<212> TYPE: DNA
<213> ORGANISM: Homo sapiens
<220> FEATURE:

<400> SEQUENCE: 9

```
aaggccatgg cggggcccga gcgctggggc ccctgctcc tgtgcctgct gcaggccgct      60
ccagggaggc cccgtctggc ccctccccag aatgtgacgc tgctctccca gaacttcagc    120
gtgtacctga catggctccc agggcttggc aaccccagg atgtgaccta ttttgtggcc     180
tatcagagct ctcccacccg tagacggtgg cgcgaagtgg aagagtgtgc gggaaccaag    240
gagctgctat gttctatgat gtgcctgaag aaacaggacc tgtacaacaa gttcaaggga    300
cgcgtgcgga cggtttctcc cagctccaag tcccctggg tggagtccga atacctggat     360
tacctttttg aagtggagcc ggccccacct gtcctggtgc tcacccagac ggaggagatc    420
ctgagtgcca tgccacgta ccagctgccc cctgcatgc ccccactgga tctgaagtat      480
gaggtggcat tctggaagga ggggggccgga aacaagaccc tatttccagt cactccccat   540
ggccagccag tccagatcac tctccagcca gctgccagcg aacaccactg cctcagtgcc    600
agaaccatct acacgttcag tgtcccgaaa tacagcaagt tctctaagcc cacctgcttc    660
ttgctggagg tcccaggact ttttctggaca cacacaccct gtggcaacct ttcagcccag   720
cagaccagag tccgtgaatg acttgttcct ctgtccccaa aaggaactga ccagaggggt    780
caggccgacg cctcgagtca gggccccagc cacccaacag acaagatgga agaaggacct    840
tgcagaggac gaagaggagg aggatgagga ggacacagaa gatggcgtca gcttccagcc    900
ctacattgaa ccaccttctt cctggggca agagcaccag gctccaggc actcggaggc     960 tggtggggtg gactcaggga ggcccagggc tcctctggtc ccaagcgaag gctcctctgc   1020
ttgggattct tcagacagaa gctgggccag cactgtggac tcctcctggg acagggctgg   1080
gtcctctggc tatttggctg agaagggggcc aggccaaggg ccgggtgggg atgggcacca  1140
agaatctctc ccaccacctg aattctccaa ggactcgggt ttcctggaag agctcccaga   1200
agataacctc tcctcctggg ccacctgggg caccttacca ccggagccga atctggtccc   1260
tgggggaccc ccagttctc ttcagacact gaccttctgc tgggaaagca gccctgagga    1320
ggaagaggag gcgagggaat cagaaattga ggacagcgat gcgggcagct gggggctga   1380 gagcacccag aggaccgagg acaggggccg acattgggg cattacatgg ccaggtgagc    1440
tgtcccccga catcccaccg aatctgatg                                    1469
```

```
<210> SEQ ID NO 10
<211> LENGTH: 244
<212> TYPE: PRT
<213> ORGANISM: Homo sapiens
<220> FEATURE:

<400> SEQUENCE: 10

Met Ala Gly Pro Glu Arg Trp Gly Pro Leu Leu Cys Leu Leu Gln
1               5                   10                  15

Ala Ala Pro Gly Arg Pro Arg Leu Ala Pro Pro Gln Asn Val Thr Leu
                20                  25                  30

Leu Ser Gln Asn Phe Ser Val Tyr Leu Thr Trp Leu Pro Gly Leu Gly
            35                  40                  45

Asn Pro Gln Asp Val Thr Tyr Phe Val Ala Tyr Gln Ser Ser Pro Thr
50                  55                  60

Arg Arg Arg Trp Arg Glu Val Glu Glu Cys Ala Gly Thr Lys Glu Leu
65                  70                  75                  80

Leu Cys Ser Met Met Cys Leu Lys Lys Gln Asp Leu Tyr Asn Lys Phe
                85                  90                  95

Lys Gly Arg Val Arg Thr Val Ser Pro Ser Ser Lys Ser Pro Trp Val
                100                 105                 110

Glu Ser Glu Tyr Leu Asp Tyr Leu Phe Glu Val Glu Pro Ala Pro Pro
            115                 120                 125

Val Leu Val Leu Thr Gln Thr Glu Glu Ile Leu Ser Ala Asn Ala Thr
            130                 135                 140

Tyr Gln Leu Pro Pro Cys Met Pro Pro Leu Asp Leu Lys Tyr Glu Val
145                 150                 155                 160

Ala Phe Trp Lys Glu Gly Ala Gly Asn Lys Thr Leu Phe Pro Val Thr
                165                 170                 175

Pro His Gly Gln Pro Val Gln Ile Thr Leu Gln Pro Ala Ala Ser Glu
            180                 185                 190

His His Cys Leu Ser Ala Arg Thr Ile Tyr Thr Phe Ser Val Pro Lys
            195                 200                 205

Tyr Ser Lys Phe Ser Lys Pro Thr Cys Phe Leu Leu Glu Val Pro Gly
210                 215                 220

Leu Phe Trp Thr His Thr Pro Cys Gly Asn Leu Ser Ala Gln Gln Thr
225                 230                 235                 240

Arg Val Arg Glu

<210> SEQ ID NO 11
<211> LENGTH: 21
<212> TYPE: DNA
<213> ORGANISM: Homo sapiens
<220> FEATURE:

<400> SEQUENCE: 11
ttcagtgtcc cgaaatacag c                                         21

<210> SEQ ID NO 12
<211> LENGTH: 20
<212> TYPE: DNA
<213> ORGANISM: Homo sapiens
<220> FEATURE:

<400> SEQUENCE: 12
aagaaggtgg ttcaatgtag                                           20
```

```
<210> SEQ ID NO 13
<211> LENGTH: 38
<212> TYPE: DNA
<213> ORGANISM: Homo sapiens
<220> FEATURE:

<400> SEQUENCE: 13
tggcagcacc atgatcaccc agttggcttc tgggacct                              38

<210> SEQ ID NO 14
<211> LENGTH: 35
<212> TYPE: DNA
<213> ORGANISM: Homo sapiens
<220> FEATURE:

<400> SEQUENCE: 14
aagactgagt tgatcaagag aatcagagcc ttaga                                 35

<210> SEQ ID NO 15
<211> LENGTH: 27
<212> TYPE: DNA
<213> ORGANISM: Homo sapiens
<220> FEATURE:

<400> SEQUENCE: 15
aatgtctaga tgctgttctc atttacc                                          27

<210> SEQ ID NO 16
<211> LENGTH: 24
<212> TYPE: DNA
<213> ORGANISM: Homo sapiens
<220> FEATURE:

<400> SEQUENCE: 16
gctccatggg acgatgccgc tgtg                                             24

<210> SEQ ID NO 17
<211> LENGTH: 20
<212> TYPE: DNA
<213> ORGANISM: Homo sapiens
<220> FEATURE:

<400> SEQUENCE: 17
gtgaaatatt gctccgtcgt                                                  20

<210> SEQ ID NO 18
<211> LENGTH: 27
<212> TYPE: DNA
<213> ORGANISM: Homo sapiens
<220> FEATURE:

<400> SEQUENCE: 18
gaagaatatt gggctttcct ggtgctg                                          27

<210> SEQ ID NO 19
<211> LENGTH: 20
<212> TYPE: DNA
<213> ORGANISM: Homo sapiens
<220> FEATURE:

<400> SEQUENCE: 19
cactgcattc tagttgtggt                                                  20
```

ISOLATED CYTOKINE RECEPTOR LICR-2

FIELD OF THE INVENTION

This invention relates to cytokine receptors. More particularly, it relates to Class II-receptors, as well as their use. A new member of the Class II cytokine receptors, referred to as "LICR-2" has been identified.

BACKGROUND AND PRIOR ART

Interleukin-10 ("IL-10" hereafter) is a major, anti-inflammatory cytokine, which was originally identified as a factor which inhibited cytokine production by activated TH1 lymphocytes. See Moore, et al, *Annu. Rev. Immunol* 19:683 (2001), incorporated by reference, for a review discussing the molecule. Following the identification of IL-10, several additional cytokines, with varying degrees of homology to IL-10 were identified. The first of these was named "mda-7", an acronym for "melanocyte differentiation associated gene 7", because its expression was upregulated during in vitro differentiation of a melanoma cell line. See Jiang, et al., *Oncogene* 11:2477 (1995). This protein exhibits 22% amino acid identity with IL-10, but it was not originally recognized as a secreted protein. Expression of mda-7 is reported to provoke irreversible growth arrest of tumors via induction of apoptosis or differentiation; however, it is not clear if this effect results from a paracrine loop that involves a classic cytokine receptor pathway, or from a cytoplasmic form of the mda-7 molecule. Recently, Schaefer, et al., *J. Immunol* 166:5859 (2001), identified the murine orthologue of mda-7, as a TH2-specific cytokine, and named it "IL-4 induced secreted protein," or "FISP." The rat counterpart, identified by Zhang, et al., *J. Biol. Chem* 275:24436 (2000), is referred to as "mob5", and is expressed by intestinal epithelial cells upon ras activation. Zhang, et al. have suggested that mob5 plays a role in ras oncogene-mediated neoplasia, through an autocrine loop involving a putative, ras-inducible cell surface receptor. Soo, et al., *J. Cell Biochem.* 74:1 (1999), have cloned the gene for mob 5and determined that it is overexpressed in the skin during wound healing.

Both the IL-10 and mda-7 genes have been mapped to chromosome 1q31–32, which is a region where two other, IL-10 related genes are found, i.e., "IL-19" and "IL-20." IL-19 is expressed by LPS activated peripheral blood mononuclear cells, as reported by Gallagher, et al., *Genes Immun* 1:442 (2000). As for IL-20, its biological activities have been studied by using transgenic mice which overexpress the cytokine, where the gene is under the control of various promoters. Such mice, as reported by Blumberg, et al., *Cell* 104:9 (2001), are characterized by neonatal lethality, and skin abnormalities, including aberrant epidermal differentiation, which is reminiscent of psoriasis lesions in humans. Blumberg, et al., have described the IL-20 receptor complex as a heterodimer of two orphan class II cytokine receptor subunits. Specifically, "CRF2–8," for which the name "IL-20Rα" has been suggested, and "DIRS1", for which "IL-20Rβ" has been suggested.

Two other genes for IL-10 homologous cytokines, i.e., "AK155" and "IL-22" are located on human chromosome 12q15, near the IFN-γ gene. AK155 is a novel cytokine which is constitutively expressed in T lymphocytes. It was found to be strongly upregulated by Herpes virus saimiri transformation of T lymphocytes. See Knappe, et al., *J. Virol* 74:3381 (2000), incorporated by reference. The authors suggest that AK155 plays a role in autocrine growth stimulation leading to spontaneous proliferation of T cells. The IL-22 molecule was originally described as an IL-9 inducible gene, and was referred to as "IL-TIF," for "IL-10 related T cell derived inducible factor." See Dumoutier, et al., *J. Immunol* 164:1814 (2000), incorporated by reference, as well as PCT Application WO 00/24758, incorporated by reference and the U.S. priority applications referred to therein. The activities of IL-22 include the induction of the acute phase response, especially in hepatocytes and they are mediated through a heterodimeric receptor which consists of the CRF2–9/IL-22R subunit, and the β chain of the IL-10 receptor. See, e.g., Dumoutier, et al., *Proc. Natl., Acad. Sci USA* 97:10144 (2000); Kotenko, et al., *J. Biol. Chem* 276: 2725 (2000); Xie, et al., *J. Biol. Chem* 275:31335 (2000), all of which are incorporated by reference. Induction of the acute phase response is associated with inflammation, allergic responses, and cancer, thus suggesting that modulation of the interaction between IL-9 and IL-22 can lead to alleviation of these conditions. In addition to its cellular receptor, IL-22 binds to a secreted member of the class II cytokine receptor family, referred to as "IL-22BP," or "IL-22 binding protein," which acts as a natural IL-22 antagonist. See Dumoutier, et al., *J. Immunol* 166:7090 (2001), Kotenko, et al., *J. Immunol* 166:7096 (2001), incorporated by reference. The 12q region, particularly the interferon γ region, has been linked to or associated with a variety of autoimmune diseases, such as multiple sclerosis, inflammatory bowel disease, rheumatoid arthritis, types I and II diabetes mellitus, allergies and asthma. This suggests that AK155 and/or IL-22 in view of the location of the genes encoding these cytokines, may be involved in one or more of these, or other, autoimmune diseases.

It will be understood from the above, that there are two classes of cytokine receptors, i.e., class I and class II. Within the class I cytokine receptors, sharing of receptor subunits is a well recognized phenomenon. Subfamilies have been defined as a result of this phenomenon, including the gp130 and IL-2R families. In the case of class II receptors, however, the only example of a shared receptor up to now has been the IL-10Rβ chain, which is involved in both IL-10 and IL-22 signaling. See Dumoutier, et al., *Proc. Natl. Acad. Sci USA* 97:10144 (2000); Kotenko, et al., *J. Biol. Chem* 276: 2725 (2000); Xie, et al., *J. Biol. Chem* 275:31335 (2000) U.S. patent application Ser. No. 09/915,735, filed Jul. 26, 2001 and incorporated by reference herein, describes members of the Class II cytokine receptor family, and a newly observed complex of two of these, i.e., IL-20Rβ and, IL-22R. It is of interest to determine the role of different class II cytokine receptors in the functions of different cytokines.

The disclosure which follows discusses the isolation and cloning of a new member of this family, referred to as "LICR-2." A ligand for this receptor has been identified as AK155. These features of the invention, as well as others, are described in the Detailed Description which follows.

DETAILED DESCRIPTION OF PREFERRED EMBODIMENTS

EXAMPLE 1

The protein sequence of IL-22BP was used for homology searching, together with TBLASTN software, to screen public libraries of the human genome sequence. A region of homology was found on chromosome 1, positioned about 25 kilobases from the site of the IL-22R gene.

The region of the genome thus identified was analyzed further, using the NIX analysis program, developed by the UK Human Genome Mapping Project Resource Center, with information at www.hgmp.mrc.ac.uk/Registered/Webapp/nix/, incorporated by reference.

The analysis suggested that the homologous sequence was a gene with 7 exons. It will be referred to as "LICR-2" hereafter.

EXAMPLE 2

The analysis programs mentioned supra suggested that the homologous region was a gene with 7 exons. A series of experiments were designed to determine the expression of the gene in various tissues. In brief, oligonucleotide probes based upon sequences found in exons 3 and 5 were prepared, i.e.:

gggaaccaag gagctgctatg (SEQ ID NO: 1), and tggcactgag gcagtggtgtt (SEQ ID NO: 2), and used in RT-PCR, following standard protocols.

The gene was found to be highly expressed in adrenal glands, kidney, heart, liver, testis, breast, skin and colon tissue. There was also good expression in lung, stomach, brain and uterine tissue.

EXAMPLE 3

Given the analysis of the gene, additional experiments were carried out to amplify the predicted mRNA. For the experiments, primers based upon exons 1 and 7, i.e., aaggccatgg cggggcccga (SEQ ID NO: 3), and cagaaggtca gtgtctgaag (SEQ ID NO: 4), were used, in RT-PCR, again using standard methods. The resulting fragment was 1424 nucleotides long, which was the expected size, based upon the primers used and the genetic analysis.

Following this work, the 3' region was amplified from liver cell line HepG2 RNA, using oligonucleotides acctgcttct tgctggaggt c (SEQ ID NO: 5)

and catcagattc ggtgggatgt c (SEQ ID NO: 6), which amplify a 951 base pair fragment extending over exons 5–7, and overlapping with the 1424 base pair fragment described supra.

Both fragments were cloned and digested by XhoI at a restriction site at nucleotide 916 from the start codon, which was present on both amplified fragments. A full length ORF was reconstituted by ligation of the two fragments into plasmid pCEP4.

The nucleotide sequence is set forth at SEQ ID NO: 7. The ORF begins 7 nucleotides from the 5' end, and extends for 1560 nucleotides. The amino acid sequence encoded by the ORF is presented at SEQ ID NO: 8. There is a potential signal peptide of approximately 20 amino acids at the N terminus, predicted using the signal P program V1.1 located at www.cbs.dtu.dk/services/SignalP, incorporated by reference. This signal peptide should be cleaved during translocation to the endoplasmic reticulum. A hydrophobic region between amino acids 229(F) and 249(W), provides indication that the molecule is a transmembrane protein, with a transmembrane domain at from about amino acid 229 to about amino acid 245.

The extracellular portion of the amino acid sequence (predicted to run from about amino acid 21 to about amino acid 228) was compared to the extracellular portions of other cytokine receptors. Highest homology was with IL-20R (24%). There was also 22% amino acid identity with IL-22BP and IL-1–20Rβ, and 21% identity with IL-22R.

There are several features which indicate that LICR-2 is a cytokine receptor. These include the hydrophobic region at the start of the open reading frame, the hydrophobic region described supra (the putative transmembrane domain), and the fact that the homology is completely within the approximately 200 amino acid extracellular domain. Also, the molecule contains several conserved amino acids seen in members of the Class II cytokine receptor family, as discussed Kotenko, et al., *Oncogene* 19(21):2557–2565 (May 15, 2000), incorporated by reference.

The functional studies described infra support the conclusion that LICR-2 is a cytokine receptor.

EXAMPLE 4

An additional set of RT-PCR experiments were carried out on HepG2 cells, using the oligonucleotides set forth at SEQ ID NOS: 5 & 6 which are located on exons 7 and 5, and allowed the amplification of a splice variant of LICR-2.

The protein translated by this splice variant lacks any transmembrane domain, suggesting it is a secreted, soluble receptor. The nucleotide sequence is set out at SEQ ID NO: 9. The ORF begins at nucleotide 7, and is 732 nucleotides long. The encoded protein is set forth at SEQ ID NO: 10.

EXAMPLE 5

Experiments were designed to check levels of expression of both LICR-2 isoforms. To do this, RT-PCR was carried out with:

ttcagtgtcc cgaaatacag c (SEQ ID NO: 11)

and aagaaggtgg ttcaatgtag (SEQ ID NO: 12)

which are located on exons 5 and 7. Following amplification, the amplification products were determined. The variants were found to be expressed simultaneously, although the transmembrane form was expressed at higher levels.

EXAMPLE 6

These experiments describe the identification of an LICR-2 ligand.

A fusion protein was made, comprising the extracellular portion of LICR-2, and the region comprising the hinge, and the CH2 and CH3 domains of murine IgG3 isotype heavy chain. This fusion protein, referred to as "LICR-2-Ig," was made by first amplifying LICR-2 using a mutated antisense primer, i.e., tggcagcacc atgatcaccc agttggcttc tgggacct (SEQ ID NO: 13), and introduced a BclI site into the stop codon. The antibody region was amplified from an anti-TNP IgG3 producing hybridoma, using:

aagactgagt tgatcaagag aatcagagccttaga (SEQ ID NO: 14)

and aatgtctaga tgctgttctc atttacc (SEQ ID NO: 15), which contain BclI and XbaI sites, for cloning. After amplification, both PCR products were digested and cloned into pCEP4, under control of the CMV promoter. The resulting clones were sequenced via standard methodologies.

HEK293-EBNA cells were seeded into 6-well plates at $3 \times 10^5$ cells/well, and cultured for one day prior to transfection with LICR-2-Ig cDNA, as described supra. Transfection was carried out via the well known lipofectamine method using 2 μg of plasmid DNA, followed by incubation of the cells in 2 ml of standard culture medium for 4 days. Supernatant was collected and used as a source of LICR-2-Ig. Supernatant collected from cells transfected with IL-10R-Ig fusion cDNA was used as a control.

Interaction analysis was carried out via ELISA. In brief, plates were coated with either recombinant AK155; Knappe, et al., *J. Virol* 74:3881–7 (2000), incorporated by reference, recombinant human IL-22, or 0.02 μg/ml of bovine serum albumin, and incubated with the test sample overnight at 4° C. The test substance, in all cases, was mixed in 20 mM Tris glycine buffer containing 30 mM NaCl, pH 9.2. After washing in PBS buffer plus Tween 20 ($1\times10^{-4}$ v/v), plates were blocked with PBS plus 1% BSA for 4 hours. 50 μl of supernatant derived from cells transfected with LICR-2 or with control supernatant referred to supra were added, and the plates were incubated for 2 hours, at 37° C. Bound LICR-2-Ig was detected using anti-murine Ig polyclonal antibodies coupled to peroxidase. The reaction was developed by adding 100 μl of TMB (1.25 mM), followed by 20 μl of $H_2SO_4$ (2M) to stop the reaction. Absorbance was measured at 450 nm.

The results indicated that supernatants from cells that were transfected with LICR-2-Ig bound AK155, but not IL-22 or BSA. Supernatants from cells transfected with IL-10R-Ig did not bind AK155, IL-22 or BSA.

These data indicate that LICR-2 is a receptor for AK155. The AK155 molecule is itself a member of the IL-10 cytokine super family, having 26% amino acid identity with IL-10, and 22.5% identity with IL-22.

EXAMPLE 7

In view of the identification of AK155 as a ligand for LICR-2, experiments were designed to determine if LICR-2 was able to transduce a signal.

A fusion protein, referred to as "IL-10R-LICR-2," comprising the extracellular portion of IL-10R and the intracellular portion of LICR-2 was produced. This fusion protein was produced by first amplifying extracellular IL-10R using:

gctccatggg acgatgccgc tgtg (SEQ ID NO: 16), and gtgaaatatt gctccgtcgt (SEQ ID NO: 17).

These mutated primers introduce an NcoI site, and an SspI site into resulting product. LICR-2 transmembrane and intracellular domains were amplified using:

gaagaatatt gggctttcct ggtgctg (SEQ ID NO: 18), and cactgcattc tagttgtggt (SEQ ID NO: 19). The former introduces an SspI site into amplification product. Amplification was carried out under standard conditions.

Following amplification, both PCR products were digested and cloned into pEF/myc/cyto plasmid under control of the EF-1 promoter. Clones were sequenced, using standard methods.

The IL-10R-LICR-2 chimeric receptor cDNA was transfected into HT-29 cells which express IL-10Rβ endogenously. A luciferase reporter gene, which is controlled by a promoter that binds STAT transcription factors, was used to analyze the response to cytokines. To do this, cells were stimulated for 2 hours with or without IL-10 or IL-22, five hours after transfection. Parental cells do not express IL-10R, and do not respond to IL-10. The IL-22 was used as a positive control, because the HT-29 cells express endogenous IL-22R, and are known to respond to IL-TIF/IL-22 by STAT activation.

After 2 hours, both IL-22 and IL-10 stimulated luciferase activity in the transfected cells to approximately the same degree, demonstrating that the cytoplasmic domain of LICR-2 can, in fact, activate STAT transcription factors.

The preceding examples disclose various aspects of this invention, including isolated nucleic acid molecules which encode LICR-2 molecules such as those with the amino acid sequence of the protein encoded by the nucleotide sequence set forth in SEQ ID NO: 7 or 9. It will be appreciated by one of ordinary skill that the degeneracy of the genetic code facilitates the preparation of nucleic acid molecules which were not be identical to the nucleotide sequence of SEQ ID NO: 7 or 9, but which encode the same protein. Of course, SEQ ID NO: 7 and 9 are preferred embodiments of this invention, but other embodiments are also a part of the invention. Genomic DNA, complementary DNA, and RNA, such as messenger RNA, are all to be included therein. Isolated nucleic acid molecules from other animal species, including other mammals, are also a part of the invention. A preferred aspect of the invention are isolated nucleic acid molecules whose complements hybridize to SEQ ID NO: 7 or 9 under stringent conditions. "Stringent conditions," as used herein, refer, for example, to hybridization at 65° C. in buffer (3.5×SSC), 0.02% Ficoll, 0.02% polyvinylpyrrolidone, 0.02% bovine serum albumin, 25 mM $NaH_2PO_4$ (pH 7), 0.1% SDS, 2 mM EDTA, followed by a final wash at 2×SSC, room temperature and then 0.1×SSC/0.2×SDS at temperatures as high as, e.g., about 65° C. More stringent conditions, such as 0.1×SSC, can also be used. These nucleic acid molecules encode proteins, such as those with amino acid sequences set forth at SEQ ID NO: 8 or 10. The receptor of this invention may be found in glycosylated or nonglycosylated, sulfated and non-sulfated forms, as well as with other post translational modifications such as, but not being limited to, acetylation, acylation, phosphorylation, palmitoylation, ubiquitination, ADP-ribosylation, hydroxylation, glucosylphophatidyl inositide addition, oxidation, reduction and so forth. Also a part of the invention are isolated nucleic acid molecules which encode proteins having 30% or more, preferably 45% or more, more preferably 50% or more, 60% or more, 70% or more, 80% or more, or 90% or more, and most preferably 95% or more amino acid identity with an amino acid sequence of a protein encoded by SEQ ID NO: 7 or 9. In systems where the signal peptide is not necessary, nucleic acid molecules lacking codons for all or part of the signal peptide may be used, and are part of the invention.

Amino acid sequence identity may be determined using the algorithm GAP (Genetics Computer Group, Madison, Wis.) or similar algorithms. GAP uses the Needleman and Wunsch algorithm to align two complete sequences and maximizes the number of matches and minimizes the number of gaps. Generally, default parameters are used, with a gap creation penalty=12 and gap extension penalty=4. Use of GAP may be preferred but other algorithms may be used, e.g. BLAST (which uses the method of Altschul, et al. (1990) *J. Mol. Biol.* 215: 405–410), FASTA (which uses the method of Pearson and Lipman (1988) PNAS USA 85: 2444–2448), or the Smith-Waterman algorithm (Smith and Waterman (1981) *J. Mol Biol.* 147: 195–197), generally employing default parameters.

Also a part of the invention are expression vectors which include the nucleic acid molecules of the invention, operably linked to a promoter, so as to facilitate expression of the DNA. It is well within the skill of the artisan to prepare such vectors.

The vectors, as well as the nucleic acid molecules per se, can be used to prepare recombinant cells, such as isolated recombinant cells, be these eukaryotic or prokaryotic, wherein either an expression vector or the nucleic acid molecule itself is incorporated therein. E. coli cells, COS cells, CHO cells, Sf9 cells, HEK293 cells, etc., are all examples of types of cells which may be used in accordance with this aspect of the invention.

Generally, nucleic acid molecules employed to produce a polypeptide or fragment thereof according to the present invention are provided as isolates, in isolated and/or purified form, or free or substantially free of material with which they are naturally associated, such as free or substantially free of nucleic acid molecules flanking the gene in the human genome, except possibly one or more regulatory sequence(s) for expression. Nucleic acid molecules may be wholly or partially synthetic and may include genomic DNA, cDNA or RNA.

Nucleic acid molecules encoding the peptides or polypeptides of the present invention can be readily prepared by the skilled person using the information and references contained herein and techniques known in the art (for example, see Sambrook and Russell "Molecular Cloning, A Laboratory Manual", Third Edition, Cold Spring Harbor Laboratory Press, 2001, and Ausubel, et al., *Current Protocols in Molecular Biology*, John Wiley and Sons, 1992, or later edition thereof).

In order to obtain expression of a nucleic acid molecule of the invention, this may be incorporated in a vector having one or more control sequences operably linked to the nucleic acid molecule to control its expression. Vectors may be chosen or constructed. These may contain appropriate regulatory sequences, including promoter sequences, terminator fragments, polyadenylation sequences, enhancer sequences, marker genes and other sequences as appropriate, e.g. nucleotide sequences so that the polypeptide or peptide is produced as a fusion and/or nucleic acid encoding secretion signals so that the polypeptide or peptide produced in the host cell is secreted from the cell. Vectors may be plasmids, viral e.g. phage, or phagemid, as appropriate. Encoded product may then be obtained by transforming the vectors into host cells in which the vector is functional, culturing the host cells so that the product is produced and recovering the product from the host cells or the surrounding medium.

A further aspect of the invention provides a method which includes introducing a nucleic acid molecule of the invention into a host cell. The introduction, which might (particularly for in vitro introduction) be generally referred to without limitation as "transformation" or "transfection", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophages. As an alternative, direct injection of the nucleic acid could be employed. Marker genes such as antibiotic resistance or sensitivity genes may be used in identifying clones containing the nucleic acid molecule of interest, as is well known in the art.

The introduction may be followed by causing or allowing expression of the nucleic acid molecule, e.g. by culturing host cells (which may include cells actually transformed although more likely the cells will be descendants of the transformed cells) under conditions for expression of the gene, so that the encoded product is produced. If the product as expressed is coupled to an appropriate signal leader peptide, it may be secreted from the cell into the culture medium. Following production by expression, a product may be isolated and/or purified from the host cell and/or culture medium, as the case may be, and subsequently used as desired, e.g. in an assay or test as disclosed herein. Note also that expression may also be carried out other systems, such as cell free, or in vitro systems, e.g. reticulocyte lysate.

Following production of a polypeptide or peptide as identified herein, it may be tested for ability to modulate binding of ligands like AK155 to LICR-2.

LICR-2 encoding nucleic acid molecules or fragments thereof may be used as probes to detect and quantify mRNAs encoding LICR-2. Assays which utilize oligonucleotide probes to detect sequences comprising all or part of a known gene sequence are well known in the art. LICR-2 mRNA levels may indicate emerging and/or existing disorders as well as the onset and/or progression of other human diseases. Therefore, assays which can detect and quantify LICR-2 mRNA may provide a valuable diagnostic tool.

Anti-sense LICR-2 RNA molecules are useful therapeutically to inhibit the translation of LICR-2 encoding mRNA where the therapeutic objective involves a desire to eliminate the presence of LICR-2 or to downregulate its levels. LICR-2 anti-sense RNA, for example, could be useful as an LICR-2 antagonizing agent in the treatment of diseases in which LICR-2 is involved in or is a causative agent, for example due to its overexpression.

Additionally, LICR-2 anti-sense RNAs are useful in elucidating LICR-2 functional mechanisms.

Another aspect of the invention is the use of fragments of the nucleic acid molecules of the invention, e.g., oligonucleotides, in assays, such as hybridization assays. The polymerase chain reaction, or "PCR" is one example of such assays, which are well known to the art. Oligonucleotides in accordance with this aspect of the invention may vary in length, but preferably consist of from 17 to 100 nucleotides, more preferably 17 to 50, and most preferably 17–25 oligonucleotides SEQ ID NOS: 1–6 are exemplary of such oligonucleotides.

A further aspect of the present invention provides a host cell containing a heterologous nucleic acid molecule encoding a polypeptide or peptide as disclosed herein. The nucleic acid molecule of the invention may be integrated into the genome (e.g. chromosome) of the host cell. Integration may be promoted by inclusion of sequences which promote recombination with the genome, in accordance with standard techniques. The nucleic acid molecule may be on an extra-chromosomal vector within the cell, or otherwise identifiably heterologous or foreign to the cell. Still another aspect of the invention relates to non-human animal models, wherein the model has been treated so as to render the gene for LICR-2 inactive. One example of such a model is a so-called "knock-out" animal, where the non-human animal may be, e.g., a rodent, such as a mouse, rat, rabbit, hamster, guinea pig, etc.

Proteins encoded by the above referenced nucleic acid molecules, preferably in isolated form, are another feature of this invention. By "protein" is meant both the immediate product of expression of the nucleic acid molecules, glycosylated or other post-traslationally modified forms of it, forms of the molecule following peptide signal cleavage, such as mature and/or processed forms of the protein, as well as multimeric forms, such as dimers, trimers, and so forth.

Also a part of the invention are multimers, such as dimers, which contain at least one protein molecule of the invention, and at least one, different, protein molecule. These multimers may be homomeric or heteromeric, such as heteromeric forms that include at least one molecule of a different soluble receptor, a transmembrane receptor, and so forth. Exemplary of the subunits which may be a part of these multimers are CRF 2–4, CRF 2–9 (IL-22R), IL-10R, IL-10Rβ, IL-20Rα, IL-20Rβ, and so forth. These molecules are all known to bind IL-10 homologous cytokines, as heterodimers. Such multimers may bind only a single specific ligand. Also a part of the invention are complexes of an LICR-2 molecule and a ligand, such as AK155 which then act as heteromeric cytokines in transmembrane receptors. Such structures parallel, e.g., the structure of IL-12. Also a feature of this invention is a protein consisting of the sequence set forth in SEQ ID NO: 8 or 10. Also included as a feature of this invention are proteins that are essentially identical to the sequence in SEQ ID NO: 8 or 10 having only conservative amino acid substitutions. Also included as a feature of the inventions are constructs, such as fusion proteins, where all or a part of the proteins described supra are linked in some fashion, e.g., to a "fusion partner" of at least one additional protein or peptide, or amino acid sequence. The "fusion partner" may be, for example, a molecule which provides a recognizable signal, either directly or indirectly, such as a FLAG peptide, β-galactosidase, luciferase, an Fc immunoglobulin, the Ig molecule portions described herein, a fluorescent protein, such as "GFP" (green fluorescent protein), and so forth. Other labels, such as radiolabels, particles, other enzymes, and metals such as gold sols, may also be used. These fusion partners are preferably joined to the molecule which is described supra at the N- and/or C-terminus of the protein; however, it is to be understood that there are many techniques known for joining molecules to amino acids, and any and all of these methodologies can produce constructs which are a part of the invention. The nucleic acid molecules encoding these fusion proteins are also part of the invention.

The proteins preferably consist of at least about 224 and no more than about 520 amino acids. More preferably, the protein consists of about 244–520, amino acids. Preferably, the amino acids sequences consist of or comprise all or part of the amino acid sequences encoded by SEQ ID NO: 8 or 10, such as proteins which lack the first 20 amino acids. Such proteins can be produced via, e.g., transforming host cells with one or more nucleic acid molecules or expression vectors in accordance with the invention, culturing the transformant, and then isolating the resulting, recombinant protein.

A "fragment" of a polypeptide generally means a stretch of amino acid residues of at least about five contiguous amino acids, often at least about seven contiguous amino acids, typically at least about nine contiguous amino acids, more preferably at least about 13 contiguous amino acids, and, more preferably, at least about 20 to 30 or more contiguous amino acids. A peptide fragment may be 5, 6, 7, 8, 9 or 10, 5 to 10, 5 to 20, 10 to 20, 10–30, 20–30, 20–40, 30–40 or more than 40 amino acids in length. For example, a fragment of LICR-2 may include a functional domain of LICR-2, may include a functional domain of LICR-2, such as an extracellular or intracellular domain, or soluble fragments which retain LICR-2 binding activity.

As noted, peptides may be made recombinantly by expression of encoding nucleic acid molecules. Peptides can also be generated wholly or partly by chemical synthesis. They can be readily prepared according to well-established, standard liquid or, preferably, solid-phase peptide synthesis methods, general descriptions of which are broadly available (see, for example, J. M. Stewart and J. D. Young, Solid Phase Peptide Synthesis, $2^{nd}$ edition, Pierce Chemical Company, Rockford, Ill. (1984), in M. Bodanzsky and A. Bodanzsky, The Practice of Peptide Synthesis, Springer Verlag, N.Y. (1984); and Applied Biosystems 430A Users Manual, ABI Inc., Foster City, Calif.), or they may be prepared in solution, by liquid phase method or by any combination of solid-phase, liquid phase and solution chemistry, e.g., by first completing the respective peptide portion and then, if desired and appropriate, after removal of any protecting groups being present, by introduction of the residue by reaction of the respective carbonic or sulfonic acid or a reactive derivative thereof.

It will be appreciated by the skilled artisan that the proteins and peptides encoded by the above recited nucleic acid molecules are a feature of the invention, and may be used to produce antibodies, in accordance with standard protocols. Such antibodies, in monoclonal and polyclonal form, constitute a further feature of the invention as do fragments of said antibodies, chimeric forms, humanized forms, recombinant forms, hybridoma cell lines which produce the antibodies and so forth.

Antibody molecules directed to LICR-2, especially a region involved in binding to AK155, are also provided as a further aspect of the present invention. Such antibody molecules are useful for inhibiting LICR-2 binding to ligands, such as AK155, and thus abrogating LICR-2 mediated activities. Similarly, the invention encompasses antibodies which inhibit formation of hetero- or homo-complexes of LICR-2 and other receptor molecules. Antibodies can also be used to purify LICR-2.

Antibody molecules may be obtained using techniques which are standard in the art. Methods of producing antibodies include immunizing a mammal (e.g. mouse, rat, rabbit, horse, goat, sheep or monkey) with the relevant polypeptide, a peptide fragment thereof, cells transfected with cDNA encoding LICR-2, or expression vectors containing LICR-2 cDNA. Antibody molecules may be obtained from immunized animals using any of a variety of techniques known in the art and screened, preferably using binding of antibody to antigen of interest. For instance, Western blotting techniques or immunoprecipitation may be used (Armitage, et al., 1992, *Nature* 357: 80–82). Isolation of antibodies and/or antibody-producing cells from an animal may be accompanied by a step of sacrificing the animal.

As an alternative or supplement to immunizing a mammal with a peptide or polypeptide, an antibody molecule may be obtained from a recombinantly produced library of expressed immunoglobulin variable domains, e.g. using lambda bacteriophage or filamentous bacteriophage which display functional immunoglobulin binding domains on their surfaces. See patent application WO92/01047, incorporated by reference for an example of this.

Antibody molecules in accordance with the present invention may be modified in a number of ways. Indeed the term "antibody molecule" should be construed as covering antibody fragments and derivatives able to bind antigen. Examples of antibody fragments capable of binding an antigen or other binding partner are the Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')$_2$ fragments, a bivalent fragment including two Fab fragments linked by a disulphide bridge at the hinge region. Single chain Fv fragments are also included.

Hybridomas capable of producing antibodies with desired binding characteristics are within the scope of the present invention, as are host cells, eukaryotic or prokaryotic, containing nucleic acid molecules encoding antibodies (including antibody fragments) and capable of their expression. The invention also provides methods of production of the antibody molecules including growing a cell capable of producing the antibody under conditions in which the antibody is produced, and preferably secreted. Such methods generally comprise isolation or purification of antibody molecules from the cells or culture medium.

The reactivities of antibody molecules with a sample may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a fusion gene encoding antibody and reporter molecule. The mode of determining binding is not a feature of the present invention and those skilled in the art are able to choose a suitable mode according to their preference and general knowledge.

Antibody molecules may also be used in purifying and/or isolating a polypeptide chain of the invention, or a peptide fragment, for instance following production of a polypeptide by expression from encoding nucleic acid molecules. Antibody molecules may be useful in a therapeutic context (which may include prophylaxis) to disrupt binding of polypeptides or other molecules with a view to inhibiting the relevant biological function or activity. In addition, antibodies which prevent ligands from binding to LICR-2, and antibodies which bind to receptor complexes which include LICR-2 are a part of the invention, as are antibodies which prevent LICR-2 from forming complexes, be these hetero or homo complexes, with other receptors molecules. Similarly, it was pointed out, supra, that LICR-2 molecules have extracellular, transmembrane, and intracellular domains. Antibodies specific to these domains or fragments of LICR-2 molecules are also a feature of the invention, as are anti-LICR antibody molecules, which can be used in, e.g., immunoassays.

Antibodies to LICR-2 may be used in the qualitative and quantitative detection of any and all forms of LICR-2, in the affinity purification of LICR-2 polypeptides, and in the elucidation of LICR-2 biosynthesis, metabolism and function. Detection of LICR-2 activity may be used as an enzymatic means of generating and amplifying a LICR-2 specific signal in such assays. Antibodies to LICR-2 may also be useful as diagnostic and therapeutic agents.

Anti-LICR-2 antibodies may be used to diagnose and quantify LICR-2 in various contexts. For example, antibodies against various domains of LICR-2 may be used as a basis for LICR-2 immunoassays or immunohistochemical assessment of LICR-2. Anti-LICR-2 antibodies may also be useful in studying the amount of LICR-2 on cell surfaces.

Antibodies may be produced which function as LICR-2 ligand agonists or antagonists whereby the regulation of LICR-2 activity becomes possible. Also, random peptides may be produced by synthetic means or be recombinant means from random oligonucleotides and the ones shown specific binding to the LICR-2 receptor may be selected with the aid of the LICR-2 extracellular domain. Such peptide segments also may be selected from a phage display library using the extracellular domain of LICR-2, using methods standard in the art. Such peptides may have agonistic or antagonistic activity. LICR-2 antibodies may also provide valuable diagnostic tools after conjugation to various compounds for in vivo imaging of LICR-2 expressing cells and tissues or tumors. For example, monoclonal antibodies against LICR-2 may be coupled either covalently or non-covalently to a suitable supramagnetic, paramagnetic, electron-dense, echogenic or radioactive agent to produce a targeted imaging agent. Antibody fragments generated by proteolysis or chemical treatments or molecules produced by using the epitope binding domains of the monoclonal antibodies could be substituted for the intact antibody. This imaging agent would then serve as a contrast reagent for X-ray, magnetic resonance, sonographic or scintigraphic imaging of the human body for diagnostic purposes.

Also a feature of the invention are immunogens, comprising all or a part of the amino acid sequence of protein molecules of the invention, preferably combined with an adjuvant, such as Complete or Incomplete Freund's Adjuvant. An immunogenic or antigenic fragment of LICR-2 useful for obtaining antibody molecules may comprise or consist of one or more epitopes of LICR-2. Linear epitopes are generally 5–8 amino acids in length, and peptides consisting of or comprising one or more epitopes or antigenic determinants of LICR-2 are provided as a further aspect of the invention. Portions of the protein sequences may be linked to other molecules, such as keyhole limpet hemocyanin, to render them more immunogenic. The domains of LICR-2 molecules, such as those discussed supra, can also be used as immunogens to prepare, e.g., domain specific antibodies.

As noted, peptides may be made recombinantly by expression of encoding nucleic acid. molecules Peptides can also be generated wholly or partly by chemical synthesis. They can be readily prepared according to well-established, standard liquid or, preferably, solid-phase peptide synthesis methods, general descriptions of which are broadly available (see, for example, J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, N.Y. (1984); and Applied Biosystems 430A Users Manual, ABI Inc., Foster City, Calif.), or they may be prepared in solution, by the liquid phase method or by any combination of solid-phase, liquid phase and solution chemistry, e.g. by first completing the respective peptide portion and then, if desired and appropriate, after removal of any protecting groups being present, by introduction of the residue by reaction of the respective carbonic or sulfonic acid or a reactive derivative thereof.

A further aspect of the present invention provides a method of obtaining an antibody directed against and preferably specific for LICR-2, the method comprising bringing a population or panel of antibody molecules of diverse binding specificity into contact with an LICR-2 polypeptide or an antigenic or immunogenic fragment thereof, and selecting one or more antibody molecules that binds the polypeptide or fragment thereof. Preferably an antibody molecule that binds the polypeptide or fragment thereof is tested for specificity of its binding for the polypeptide or fragment thereof, e.g. by testing binding on a panel of unrelated antigens, for example by ELISA as is standard in the art. Preferably an antibody molecule specific for LICR-2 is identified.

A population of antibody molecules may for example be provided as a phage display library and brought into contact with the polypeptide or fragment thereof in vitro. Another of the various options available to the skilled person is to administer a peptide or polypeptide to a mammal in order to raise an immune response. Antibody molecules and/or cells producing antibody molecules can be taken or harvested from the animal or its serum, and tested for the desired property or properties.

Once obtained, an antibody molecule can be formulated into a composition comprising at least one additional component, such as a pharmaceutically acceptable excipient or carrier, and may be used as desired.

As noted, antibody molecules can be used, e.g., to determine if the proteins of the invention are present. This is a further feature of the invention, as is explained elsewhere herein.

It has been shown, in the examples, that the nucleic acid molecules of the invention encode proteins that bind to AK155. Hence, a further feature of the invention is a method of inhibiting AK155 activity, by contacting a sample with an amount of the protein of this invention sufficient to inhibit or block the activity of AK155. Especially, preferred are soluble forms of LICR-2, such as molecules encoded by all or a part of SEQ ID NO: 10.

One could also use the molecules of the invention to test the efficacy of AK155 agonists or antagonists when administered to a subject. Thus, a further aspect of the invention is a method to determine activity of endogenous AK155, such as in situations where excess AK155 activity is implicated. One can also block or inhibit AK155 activity by blocking or inhibiting LICR-2 activity, using the molecules of this invention, such as antibodies. The ability to regulate AK155 activity is important in conditions such as autocrine growth stimulation.

As noted, LICR-2 fragments that inhibit binding of AK155 to the receptor may be used, as may antibody molecules, and small molecules or other agents identified using, for example, an assay of the invention as disclosed herein. Accordingly, disclosure of aspects of the invention making use of LICR-2 in therapeutic, prophylactic or diagnostic contexts should be taken as disclosure of analogous aspects of the invention making use of any one or more of an LICR-2 fragment or fragments, an antibody molecule that binds and preferably is specific for LICR-2, especially an antibody molecule that affects binding of LICR-2 to AK155, and an agent identified using an assay of the invention, able to modulate LICR-2 binding to AK155.

Whether a protein, polypeptide, peptide, antibody molecule, small molecule or other substance is to be employed for a therapeutic purpose, e.g. in treatment of a condition identified herein, in various further aspects, the present invention further provides a pharmaceutical composition, medicament, drug or other composition for such a purpose, the composition comprising one or more such substances, the use of such a substance in a method of medical treatment, a method comprising administration of such a substance to a patient, e.g. for treatment (which may include preventative treatment) of a medical condition, use of such a substance in the manufacture of a composition, medicament or drug for administration for such a purpose, e.g. for treatment of a medical condition, and a method of making a pharmaceutical composition comprising admixing such a substance with a pharmaceutically acceptable excipient, vehicle or carrier, and optionally other ingredients.

Whatever the substance used in a method of medical treatment of the present invention, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution or aerosol which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Examples of techniques and protocols mentioned above can be found in Remington's Pharmaceutical Sciences, 16th edition, Osol, A. (ed), 1980.

Instead of administering such substances directly, they may be produced in target cells by expression from an encoding nucleic acid introduced into the cells, e.g. from a viral vector or as "naked" DNA administered to the body. Nucleic acid encoding the substance e.g. a peptide able to modulate, e.g. interfere with, the interaction of LICR-2 and AK155, may thus be used in methods of gene therapy, for instance in treatment of individuals, e.g. with the aim of preventing or curing (wholly or partially) a disorder.

A polypeptide or peptide of the invention can be used in assaying for agents and substances that bind to LICR-2 polypeptide or have a stimulating or inhibiting effect on the expression and/or activity of LICR-2. In addition, the polypeptide or peptide of the invention can also be used to assay for agents that, by affecting the association or interaction between LICR-2 and AK155, modulate AK155 function in vivo. Formats that may be used in such assays are described in detail below, and may comprise determining binding between components in the presence or absence of a test substance and/or determining ability of a test substance to modulate a biological or cellular function or activity in which binding of LICR-2 to AK155 plays a role. Assay methods that involve determination of binding between components and the effect of a test substance on such binding need not necessarily utilize full-length wild-type polypeptide chains. For instance, fragments of LICR-2, such as the extracellular domain that retain ability to bind AK155 may be employed, and vice versa. Indeed, as discussed further below, fragments of the polypeptides themselves represent a category of putative inhibitors, that may be used to interfere with binding between polypeptides. Fusion proteins may also be used in such assays.

Examples of agents, candidate compounds or test compounds include, but are not limited to, nucleic acids (e.g., DNA and RNA), carbohydrates, lipids, proteins, peptides, peptidomimetics, small molecules and other drugs. Agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, *Anticancer Drug Des.* 12:145; U.S. Pat. No. 5,738,996; and U.S. Pat. No. 5,807,683, each of which is incorporated herein in its entirety by reference).

Examples of methods for the synthesis of molecular libraries can be found in the art, for example: DeWitt, et al., 1993, *Proc. Natl. Acad. Sci. USA* 90:6909; Erb, et al., 1994, *Proc. Natl. Acad. Sci. USA* 91:11422; Zuckermann, et al., 1994, *J. Med. Chem.* 37:2678; Cho, et al., 1993, *Science* 261:1303; Carrell, et al.,1994, *Angew. Chem. Into. Ed. Engl.* 33:2059; Carrell, et al.,1994, *Angew. Chem. Into. Ed. Engl.* 33:2061; and Gallop, et al., 1994, *J. Med. Chem.* 37:1233, each of which is incorporated herein in its entirety by reference.

Libraries of compounds may be presented, e.g., presented in solution (e.g., Houghten, 1992, *Bio/Techniques* 13:412–421), or on beads (Lam, 1991, *Nature* 354:82–84), chips (Fodor, 1993, *Nature* 364:555–556), bacteria (U.S. Pat. No. 5,223,409), spores (U.S. Pat. Nos. 5,571,698; 5,403,484; and 5,223,409), plasmids (Cull, et al., 1992, *Proc. Natl. Acad. Sci. USA* 89:1865–1869) or phage (Scott and Smith, 1990, *Science* 249:386–390; Devlin, 1990, *Science* 249:404–406; Cwirla, et al., *Proc. Natl. Acad. Sci. USA* 87:6378–6382; and Felici, 1991, *J. Mol. Biol.* 222:301–310), each of which is incorporated herein in its entirety by reference.

The use of peptide libraries may be preferred in certain circumstances. The potential for binding between polypeptide chains of receptors of the invention to be inhibited by means of peptide fragments of the polypeptide chains has been mentioned already. Such peptide fragments may consist of for example 10–40 amino acids, e.g. about 10, about 20, about 30 or about 40 amino acids, or about 10–20, 20–30 or 30–40 amino acids. These may be synthesized recombinantly, chemically or synthetically using available techniques.

In any assay method according to the invention, the amount of test substance or compound which may be added to an assay of the invention will normally be determined by trial and error depending upon the type of compound used. Even a molecule which has a weak effect may be a useful lead compound for further investigation and development.

For example, the fact that domains of LICR-2 do in fact participate in STAT activation, e.g., STAT phosphorylation, suggests that one can assess such agents by measuring STAT activation/phosphorylation. Methods for measuring these phenomena are known to the art and include, e.g., immunoassays using antibodies specific for phosphorylated forms of STAT molecules, and/or reporter gene systems, such as luciferase under control of a STAT-regulated promoter or promoters, and/or monitoring expression of endogenous genes regulated by one or moe STAT molecules.

An additional type of assay which can be used combines the extracellular domain of the LICR-2 molecules of the invention or equivalents thereof with cytoplasmic domains of the EpoR receptor. The relevant molecules, as described supra are combined with the hybrid molecules, and cell proliferation is measured. Increased, proliferation is indicative of the presence of a ligand and/or against of the LICR-2 molecules. In this, as in assays, it is of course necessary to run a control together with the assay.

In one embodiment, agents that interact with (i.e., bind to) an LICR-2 molecule of the invention are identified in a cell-based assay system. In accordance with this embodiment, cells expressing an LICR-2 molecule, or a fragment of an LICR-2 molecule or an LICR-2 fusion protein are contacted with a candidate compound or a control compound and the ability of the candidate compound to interact with LICR-2 is determined. If desired, this assay may be used to screen a plurality (e.g., a library) of candidate compounds. The cell, for example, can be of prokaryotic origin (e.g., *E. coli*) or eukaryotic origin (e.g., yeast or mammalian). Further, the cells can express an LICR-2 molecule, a fragment of LICR-2 or an LICR-2 fusion protein endogenously or be genetically engineered to express an LICR-2 molecule, a fragment of LICR-2, or an LICR-2 fusion protein. In certain instances, the LICR-2 molecule, fusion protein or fusion protein or the candidate compound is labeled, for example with a radioactive label (such as $^{32}$P, $^{35}$S, $^{131}$I or $^{90}$Yt) or a fluorescent label(such as fluorescein isothiocyanate, rhodamine, phycoerythrin, phycocyanin, allophycocyanin, o-phthaldehyde or fluorescamine) to enable detection of an interaction between LICR-2 and a candidate compound. The ability of the candidate compound to interact directly or indirectly with an LICR-2 molecule, a fragment of LICR-2 or an LICR-2 fusion protein can be determined by methods known to those of skill in the art. For example, the interaction between a candidate compound and an LICR-2 molecule, a fragment of LICR-2, or an LICR-2 fusion protein can be determined by flow cytometry, a scintillation assay, immunoprecipitation or Western blot analysis.

In another embodiment, agents that interact with (i.e., bind to) an LICR-2 molecule, an LICR-2 fragment (e.g., a functionally active fragment) or an LICR-2 fusion protein are identified in a cell-free assay system. In accordance with this embodiment, a native or recombinant LICR-2 molecule or fragment thereof, or an LICR-2 fusion protein or fragment thereof, is contacted with a candidate compound or a control compound and the ability of the candidate compound to interact with the LICR-2 molecule or LICR-2 fusion protein is determined. If desired, this assay may be used to screen a plurality (e.g., a library) of candidate compounds. Preferably, the LICR-2 molecule, LICR-2 fragment or the LICR-2 fusion protein is first immobilized, by, for example, contacting said LICR-2 molecule, fragment or fusion protein with an immobilized antibody which specifically recognizes and binds it, or by contacting a purified preparation of said LICR-2 molecule, fragment or fusion protein with a surface designed to bind proteins. The LICR-2 molecule, or LICR-2 fragment or LICR-2 fusion protein may be partially or completely purified (e.g., partially or completely free of other polypeptides) or part of a cell lysate. Further, the LICR-2 molecule or LICR-2 fragment may be a fusion protein comprising LICR-2 or a biologically active portion thereof, and a domain such as glutathionine-S-transferase.

Alternatively, the LICR-2 molecule, LICR-2 fragment or LICR-2 fusion protein can be biotinylated using techniques well known to those of skill in the art (e.g., biotinylation kit, Pierce Chemicals; Rockford, Ill.). The ability of the candidate compound to interact with an LICR-2 molecule, LICR-2 fragment or LICR-2 fusion protein can be can be determined by methods known to those of skill in the art.

In another embodiment, a cell-based assay system is used to identify agents that bind to or modulate the activity of a protein, such as an enzyme, or a biologically active portion thereof, which is responsible for the production or degradation of an LICR-2 molecule or is responsible for the post-translational modification of an LICR-2 molecule. In a primary screen, a plurality (e.g., a library) of compounds are contacted with cells that naturally or recombinantly express: (i) an LICR-2 molecule, an isoform of an LICR-2 molecule, an LICR-2 fusion protein, or a biologically active fragment of any of the foregoing; and (ii) a protein that is responsible for processing of an LICR-2 molecule in order to identify compounds that modulate the production, degradation, or post-translational modification of LICR-2. If desired, compounds identified in the primary screen can then be assayed in a secondary screen against cells naturally or recombinantly expressing the specific LICR-2 of interest. The ability of the candidate compound to modulate the production, degradation or post-translational modification of an LICR-2 molecule can be determined by methods known to those of skill in the art, including without limitation, flow cytometry, a scintillation assay, immunoprecipitation and Western blot analysis.

In another embodiment, agents that competitively interact with (i.e., bind to) an LICR-2 polypeptide are identified in a competitive binding assay. In accordance with this embodiment, cells expressing an LICR-2 polypeptide, LICR-2 fragment, or an LICR-2 fusion protein are contacted with a candidate compound and a compound known to interact with LICR-2, for example, AK155; the ability of the candidate compound to competitively interact with said LICR-2 polypeptide, or LICR-2 fragment, is then determined. Alternatively, agents that competitively interact with (i.e., bind to) an LICR-2 polypeptide, LICR-2 fragment, or LICR-2 fusion protein are identified in a cell free system by contacting an LICR-2 polypeptide, LICR-2 fragment or LICR-2 fusion protein with a candidate compound and a compound known to interact with said LICR-2 polypeptide, LICR-fragment or LICR-2 fusion protein. As stated above, the ability of the candidate compound to interact with an LICR-2 polypeptide, LICR-fragment or LICR-2 fusion protein can be determined by methods known to those of skill in the art. These assays, whether cell-based or cell-free, can be used to screen a plurality (e.g., a library) of candidate compounds.

In a preferred embodiment agents that competitively interact with an LICR-2 polypeptide are identified in a cell-free assay system by contacting an LICR-2 polypeptide an LICR-2 fragment or LICR-2 fusion protein with a candidate compound in the presence or absence of AK155.

In another embodiment, agents that modulate (i.e., upregulate or downregulate) the expression of an LICR-2 polypeptide are identified by contacting cells (e.g., cells of prokaryotic origin or eukaryotic origin) expressing an LICR-2 polypeptide with a candidate compound or a control compound (e.g., phosphate buffered saline (PBS)) and determining the expression of an LICR-2 polypeptide, or mRNA encoding an LICR-2 polypeptide. The level of expression of a selected LICR-2 polypeptide or mRNA encoding of LICR-2 polypeptide, in the presence of the candidate compound is compared to the level of expression of an LICR-2 polypeptide or mRNA encoding an LICR-2 polypeptide in the absence of the candidate compound (e.g., in the presence of a control compound). The candidate compound can then be identified as a modulator of the expression of an LICR-2 polypeptide based on this comparison. For example, when expression of LICR-2 is significantly greater in the presence of the candidate compound than in its absence, the candidate compound is identified as a stimulator of expression of LICR-2. Alternatively, when expression of LICR-2 is significantly less in the presence of the candidate compound than in its absence, the candidate compound is identified as an inhibitor of the expression of LICR-2. The level of expression of LICR-2 or the mRNA that encodes it can be determined by methods known to those of skill in the art. For example, mRNA expression can be assessed by Northern blot analysis or RT-PCR, and protein levels can be assessed by Western blot analysis.

In another embodiment, agents that modulate the activity of an LICR-2 polypeptide are identified by contacting a preparation containing an LICR-2 polypeptide, or cells (e.g., prokaryotic or eukaryotic cells) expressing an LICR-2 polypeptide with a test compound or a control compound and determining the ability of the test compound to modulate (e.g., stimulate or inhibit) the activity of said LICR-2 polypeptide. The activity of an LICR-2 polypeptide can be assessed by detecting induction of a cellular signal transduction pathway of an LICR-2 polypeptide (e.g., intracellular Ca2+, diacylglycerol, IP3, STAT activation etc.), detecting catalytic or enzymatic activity of the target on a suitable substrate, detecting catalytic or enzymatic activity of the target on a suitable substrate, detecting the induction of a reporter gene (e.g., a regulatory element that is responsive to an LICR-2 polypeptide and is operably linked to a nucleic acid encoding a detectable marker, e.g., luciferase), or detecting a cellular response, for example, cellular differentiation, or cell proliferation. Based on the present description, techniques known to those of skill in the art can be used for measuring these activities (see, e.g., U.S. Pat. No. 5,401,639, which is incorporated herein by reference). The candidate compound can then be identified as a modulator of the activity of an LICR-2 polypeptide by comparing the effects of the candidate compound to the control compound. Suitable control compounds include phosphate buffered saline (PBS) and normal saline (NS).

In another embodiment, agents that modulate (i.e., upregulate or downregulate) the expression, activity or both the expression and activity of an LICR-2 polypeptide are identified in an animal model. Examples of suitable animals include, but are not limited to, mice, rats, rabbits, monkeys, guinea pigs, dogs and cats. Preferably, the animal used represents a model of autoimmune diseases. In accordance with this embodiment, the test compound or a control compound is administered (e.g., orally, rectally or perenterally such as intraperitoneally or intravenously) to a suitable animal and the effect on the expression, activity or both expression and activity of LICR-2 polypeptide is determined. Changes in the expression of an LICR-2 polypeptide can be assessed by the methods outlined above.

An LICR-2 polypeptide can be used as a "bait protein" in a two-hybrid assay or a three-hybrid assay to identify other proteins, including natural ligands, that bind to or interact with an LICR-2 polypeptide.

For example, an LICR-2 polypeptide of the invention may be fused to a DNA binding domain such as that of the yeast transcription factor GAL4. The GAL4 transcription factor includes two functional domains. These domains are the DNA binding domain (GAL4DBD) and the GAL4 transcriptional activation domain (GAL4TAD). By fusing a first polypeptide component of the assay to one of those domains, and a second polypeptide component of the assay to the respective counterpart, a functional GAL4 transcription factor is restored only when the two polypeptides interact. Thus, interaction of these polypeptides may be measured by the use of a reporter gene linked to a GAL4 DNA binding site which is capable of activating transcription of said reporter gene.

This two hybrid assay format is described by Fields and Song, 1989, *Nature* 340: 245–246. It can be used in both mammalian cells and in yeast. Other combinations of DNA binding domain and transcriptional activation domain are available in the art and may be preferred, such as the LexA DNA binding domain and the VP60 transcriptional activation domain.

As those skilled in the art will appreciate, such binding proteins are likely to be involved in the propagation of signals by LICR-2 polypeptides of the invention, including upstream or downstream elements of a signalling pathway involving the LICR-2 polypeptides of the invention.

The precise format of any of the screening or assay methods of the present invention may be varied by those of skill in the art using routine skill and knowledge. The skilled person is well aware of the need to employ appropriate control experiments.

Performance of an assay method according to the present invention may be followed by isolation and/or manufacture and/or use of a compound, substance or molecule which tests positive for ability to modulate the relevant interaction or affect the relevant biological function or activity. Following identification of a suitable agent, it may be investigated further, and may be modified or derivatized to alter one or more properties, without abolishing its ability to modulate the relevant interaction or affect the relevant biological function. For instance, a single chain Fv antibody molecule may be reformatted into a whole antibody comprising antibody constant regions, e.g. an IgG antibody. Any peptidyl molecule may be modified by addition, substitution, insertion or deletion of one or more amino acids, or by joining of an addition moiety or protein domain. An active agent may be subject to molecular modelling in silico and one or more mimetics of the originally identified agent may be created.

Furthermore, an active agent of the invention may be manufactured and/or used in preparation, i.e., manufacture or formulation, of a composition such as a medicament, pharmaceutical composition or drug. These may be administered to individuals, as discussed.

A compound, whether a peptide, antibody, small molecule or other substance found to have the ability to affect binding between polypeptide chains of a receptor of the invention or binding of such a receptor to a ligand has therapeutic and other potential in a number of contexts. For therapeutic treatment such a compound may be used in combination with any other active substance.

Generally, such a substance identified according to the present invention and to be subsequently used is provided in an isolated and/or purified form, i.e. substantially pure. This may include being in a composition where it represents at least about 90% active ingredient, more preferably at least about 95%, more preferably at least about 98%. Such a composition may, however, include inert carrier materials or other pharmaceutically and physiologically acceptable excipients. Thus, a composition may consist of the active ingredient obtained using the invention, and an inert carrier. Furthermore, a composition according to the present invention may include in addition to a modulator compound as disclosed, one or more other molecules of therapeutic use.

Also a part of this invention is a method for determining the presence of the receptor-like antagonist of this invention in a tissue or cell sample comprising contacting said sample with an antibody specific for said receptor-like antagonist and determining binding therebetween. Methods for determining the binding of an antibody and its antigen are well known to those of skill in the art and need not be elaborated herein.

The receptor protein of this invention may also be used to determine the presence of AK155 in a sample by, e.g., labeling said receptor-like binding protein and then contacting said sample with said receptor-like antagonist and determining binding therebetween wherein said binding is indicative of the presence of AK155. Alternatively, one may determine the presence of AK155 in a sample by treating a cell line that is responsive to AK155 to two aliquots of said sample, one containing the receptor-like binding protein and one without the receptor-like binding protein, then measuring and comparing the response of said responsive cell to the two aliquots wherein a difference in response to the two aliquots is indicative of the presence of AK155. In the alternative, cells that are responsive to AK155 can be used in such assays. To elaborate, cells which show some type of response to AK155, can be used to screen for presence and/or amount of LICR-2 in a sample. For example, assuming that the cell is incubated in the sample in question together with LICR-2, any observed change in the response, is indicative of LICR-2 in said sample. The situation seems to be analogous for HVS, in which the overexpression of ak155 is one of rare changes between native and transformed T cells. AK155 is a good candidate to play a role in the autocrine growth stimulation leading to spontaneous proliferation of T cells after HVS infection.

The soluble LICR-2 molecules described herein are further examples of soluble, cytokine receptors generated in vivo. See, e.g. Rose-John, et al., *Biochem J.* 300: 281 (1994); Fernandez-Botran, et al., *Adv. Immunol* 63:269 (1996). Heaney, et al., *Blood* 87: 845 (1996). Soluble cytokine receptors compete with cell surface receptors for binding to free or unbound cytokine molecules. With the exception of IL-6R, this binding prevents cytokines from reaching the cell membrane and generating a signal. The binding is generally reversible, leading to temporary sequestration of the cytokine from membrane receptors. Soluble cytokine receptors also enhance the activity of cytokines by increasing their stability, decreasing proteolytic degradation, or reducing clearance. Such functions, i.e., as cytokine carriers in vivo, are seen to help potentate the systemic effect of cytokines, with the antagonistic effect being pertinent to paracrine and autocrineculture medium activities. Proteins of the invention may be used to manufacture medicaments for treating AK155 mediated disease. Further, one can carry out assays for agents which moderate the binding of proteins in accordance with the invention, by contacting an AK155 polypeptide or fragment with a protein of the invention or a fragment thereof, and a test substance, under conditions in which where the test substance is not an inhibitor of binding of the protein to AK155, the protein or fragment thereof binds the AK155 polypeptide or fragment thereof. The binding of the Class II-cytokine receptor polypeptide or fragment thereof to the AK155 polypeptide or fragment thereof is then determined, to identify agents which modulate binding. One can add an additional step to the assay, by testing the agent for its ability to modulate an AK155 mediated activity. Further, the agent can be formulated into a composition with one or more additional components, such as into a medicament useful in treating an AK155-mediated disorder. The AK155 or cytokine receptor binding protein can be contacted with the putative binding modulating agent either in vitro or in vivo, such as via administrating the material to an agent in need thereof. The agent may be an antibody molecule, but other materials, such as peptide fragments of AK155, or proteins of the invention, may also be used.

Other features of the invention will be clear to the artisan and need not be discussed further.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An isolated nucleic acid molecule which encodes a cytokine receptor, which binds to AK155 and induces STAT activation wherein the complementary nucleotide sequence of said isolated nucleic acid molecule, hybridizes, under stringent conditions, to SEQ ID NO: 7 or SEQ ID NO: 9, wherein said straingent conditions are defined as hybridization at 65° C. in 3.5×SSC, 0.02% Ficoll, 0.02% polyvinylpyrrolidine, 0.02% bovine serum albumin, 25 mM $NaH_2PO_4$ (pH 7), 0.1% SDS, 2 mM EDTA, and a final wash at room temperature with 2×SSC, followed by a wash at 0.1'SSC/0.2×SDS at a temperature as high as 65° C.

2. The isolated nucleic acid molecule of claim 1, wherein said isolated nucleic acid molecule encodes a protein, the amino acid sequence of which is set forth in SEQ ID NO: 8 or SEQ ID NO: 10.

3. The isolated nucicic acid molecule of claim 1, comprising the nucleotide sequence set forth at SEQ ID NO: 7 or SEQ ID NO: 9.

4. Expression vector comprising the isolated nucleic acid molecule of claim 1, operably linked to a promoter.

5. Expression vector comprising the isolated nucleic acid molecule of claim 2, operably linked to a promoter.

6. Expression vector comprising the isolated nucleic acid molecule of claim 3, operably linked to a promoter.

7. Recombinant cell line or cell strain, transformed or transfected with the isolated nucleic acid molecule of claim 1.

8. Recombinant cell line or cell strain, transformed or tratisfected with the isolated nucleic acid molecule of claim 2.

9. Recombinant cell line or cell strain, transformed or transfected with the isolated nucleic acid molecule of claim 3.

10. Recombinant cell line or cell strain, transformed or transfected with the expression vector of claim 4.

11. Recombinant cell line or cell strain, transformed or transfected with the expression vector of claim 5.

12. Recombinant cell line or cell strain, transformed or transfected with the expression vector of claim 6.

13. A method for producing a cytokine receptor comprising transforming or transfecting a cell with the isolated nucleic acid molecule of claim 1, culturing the thus transformed or transfected cell in culture medium to produce said cytokine receptor, end isolating it from said cell or culture medium.

14. A method for producing a cytokine receptor, comprising transforming or transfecting a cell with the expression vector of claim 4, culturing the thus transformed or transfected cell in culture medium to produce said soluble cytokine receptor, and isolating it from said cell or culture medium.

15. An isolated oligonucleotide consisting of 17 to 100 contiguous nucleotides of the nucleotide sequence set forth in SEQ ID NO: 7, or SEQ ID NO: 9.

* * * * *